US 8,560,063 B2

(12) United States Patent
Ideker et al.

(10) Patent No.: US 8,560,063 B2
(45) Date of Patent: *Oct. 15, 2013

(54) POST-DEFIBRILLATION PACING METHODS AND DEVICES

(75) Inventors: Raymond E. Ideker, Birmingham, AL (US); Gregory P. Walcott, Wilsonville, AL (US)

(73) Assignee: UAB Research Foundation, Birmingham, AL (US)

( * ) Notice: Subject to any disclaimer, the term of this patent is extended or adjusted under 35 U.S.C. 154(b) by 2357 days.

This patent is subject to a terminal disclaimer.

(21) Appl. No.: 10/238,343

(22) Filed: Sep. 10, 2002

(65) Prior Publication Data

US 2004/0049232 A1 Mar. 11, 2004

(51) Int. Cl.
*A61N 1/00* (2006.01)

(52) U.S. Cl.
USPC .................................................. 607/4

(58) Field of Classification Search
USPC .................................................. 607/4
See application file for complete search history.

(56) References Cited

U.S. PATENT DOCUMENTS

| | | | |
|---|---|---|---|
| 3,825,015 A | 7/1974 | Berkovits | 128/404 |
| 3,995,623 A | 12/1976 | Blake et al. | 128/2.06 E |
| 4,355,646 A | 10/1982 | Kallok et al. | 128/786 |
| 4,365,639 A | 12/1982 | Goldreyer | 128/786 |
| 4,444,195 A | 4/1984 | Gold | 128/642 |
| 4,499,907 A | 2/1985 | Kallok et al. | 128/786 |
| 4,559,946 A | 12/1985 | Mower | 128/419 D |
| 4,567,901 A | 2/1986 | Harris | 128/786 |
| 4,637,397 A | 1/1987 | Jones et al. | 128/419 D |
| 4,643,201 A | 2/1987 | Stokes | 128/786 |
| 4,693,253 A | 9/1987 | Adams | 128/419 D |
| 4,708,145 A | 11/1987 | Tacker, Jr. et al. | 128/419 D |
| 4,735,206 A * | 4/1988 | Hewson | 607/4 |
| 4,800,883 A | 1/1989 | Winstrom | 128/419 D |
| 4,850,357 A | 7/1989 | Bach, Jr. | 128/419 D |
| 4,901,725 A | 2/1990 | Nappholz et al. | 128/419 |

(Continued)

FOREIGN PATENT DOCUMENTS

| EP | 0095726 B1 | 2/1988 |
|---|---|---|
| EP | 0472 411 A1 | 2/1992 |

(Continued)

OTHER PUBLICATIONS

International Search Report for International Application PCT/US03/22263 filed Jul. 16, 2003 (date of mailing Nov. 28, 2003).

(Continued)

*Primary Examiner* — Mark W Bockelman
(74) *Attorney, Agent, or Firm* — Myers Bigel Sibley & Sajovec, PA

(57) ABSTRACT

Methods, systems and computer program products for cardiac pacing are provided. A defibrillation shock is applied to a heart of the patient and a pacing stimulation signal is automatically applied to the heart of the patient subsequent to termination of the delivery of the defibrillation shock. The pacing stimulation may be applied to the heart of the patient within about two seconds of termination of the defibrillation shock. The pacing stimulation signal may be applied to the heart of the patient subsequent to termination of the defibrillation shock irrespective of a characterization of electrical activity detected in the heart. The pacing stimulation may be single and/or paired pacing stimulation.

74 Claims, 6 Drawing Sheets

(56) References Cited

U.S. PATENT DOCUMENTS

| | | | | |
|---|---|---|---|---|
| 4,928,688 A | 5/1990 | Mower | | 128/419 |
| 5,107,834 A | 4/1992 | Ideker et al. | | 128/419 D |
| 5,165,403 A | 11/1992 | Mehra | | 128/419 |
| 5,184,616 A | 2/1993 | Weiss | | 128/419 |
| 5,201,808 A | 4/1993 | Steinhaus et al. | | 128/419 |
| 5,209,229 A | 5/1993 | Gilli | | 128/419 |
| 5,224,476 A | 7/1993 | Ideker et al. | | 128/419 D |
| 5,230,337 A | 7/1993 | Dahl et al. | | 607/5 |
| 5,235,977 A | 8/1993 | Hirschberg et al. | | 607/5 |
| 5,235,978 A | 8/1993 | Hirschberg et al. | | 607/5 |
| 5,251,624 A | 10/1993 | Bocek et al. | | 607/6 |
| 5,267,559 A | 12/1993 | Jin et al. | | 128/419 D |
| 5,269,298 A | 12/1993 | Adams et al. | | 128/419 D |
| 5,269,319 A | 12/1993 | Schulte et al. | | 128/786 |
| 5,282,836 A | 2/1994 | Kreyenhagen et al. | | 607/4 |
| 5,292,338 A | 3/1994 | Bardy | | 607/5 |
| 5,303,702 A | 4/1994 | Bonnet et al. | | 607/20 |
| 5,304,139 A | 4/1994 | Adams et al. | | 607/122 |
| 5,304,218 A | 4/1994 | Alferness | | 607/122 |
| 5,312,444 A | 5/1994 | Bocek et al. | | 607/5 |
| 5,313,953 A | 5/1994 | Yomtov et al. | | 600/508 |
| 5,314,430 A | 5/1994 | Bardy | | 607/5 |
| 5,324,309 A | 6/1994 | Kallok | | 607/5 |
| 5,328,442 A | 7/1994 | Levine | | |
| 5,331,966 A | 7/1994 | Bennett et al. | | 128/696 |
| 5,332,400 A | 7/1994 | Alferness | | 607/5 |
| 5,344,430 A | 9/1994 | Berg et al. | | 607/8 |
| 5,348,021 A | 9/1994 | Adams et al. | | 128/708 |
| 5,350,402 A | 9/1994 | Infinger et al. | | 607/5 |
| 5,366,485 A | 11/1994 | Kroll et al. | | 607/5 |
| 5,366,486 A | 11/1994 | Zipes et al. | | 607/5 |
| 5,387,233 A | 2/1995 | Alferness et al. | | 607/126 |
| 5,395,373 A | 3/1995 | Ayers | | 607/8 |
| 5,403,351 A | 4/1995 | Saksena | | 607/4 |
| 5,403,354 A | 4/1995 | Adams et al. | | 607/5 |
| 5,405,375 A | 4/1995 | Ayers et al. | | 607/122 |
| 5,411,527 A | 5/1995 | Alt | | 607/5 |
| 5,417,717 A | 5/1995 | Salo | | |
| 5,423,772 A | 6/1995 | Lurie et al. | | 607/282 |
| 5,431,681 A | 7/1995 | Helland | | 607/4 |
| 5,431,682 A | 7/1995 | Hedberg | | 607/5 |
| 5,431,683 A | 7/1995 | Bowald et al. | | 607/5 |
| 5,433,729 A | 7/1995 | Adams et al. | | 607/5 |
| 5,433,730 A | 7/1995 | Alt | | 607/5 |
| 5,441,519 A | 8/1995 | Sears | | 607/5 |
| 5,443,491 A | 8/1995 | Snichelotto | | 607/122 |
| 5,447,519 A | 9/1995 | Peterson | | 607/5 |
| 5,456,706 A | 10/1995 | Pless et al. | | 607/122 |
| 5,464,429 A | 11/1995 | Hedberg et al. | | 607/4 |
| 5,464,432 A | 11/1995 | Infinger et al. | | 607/5 |
| 5,470,348 A | 11/1995 | Neubauer et al. | | 607/68 |
| 5,476,498 A | 12/1995 | Ayers | | 607/122 |
| 5,476,499 A | 12/1995 | Hirschberg | | 607/123 |
| 5,486,199 A | 1/1996 | Kim et al. | | 607/5 |
| 5,487,753 A | 1/1996 | MacCarter et al. | | 607/17 |
| 5,489,293 A | 2/1996 | Pless et al. | | 607/5 |
| 5,522,853 A | 6/1996 | Kroll | | 607/5 |
| 5,531,764 A | 7/1996 | Adams et al. | | 607/5 |
| 5,554,176 A | 9/1996 | Maddison et al. | | 607/9 |
| 5,560,369 A | 10/1996 | McClure et al. | | 128/704 |
| 5,578,064 A | 11/1996 | Prutchi | | 607/19 |
| 5,584,865 A | 12/1996 | Hirschberg et al. | | 607/5 |
| 5,609,621 A | 3/1997 | Bonner | | 607/122 |
| 5,620,471 A | 4/1997 | Duncan | | 607/4 |
| 5,645,569 A * | 7/1997 | Ayers | | 607/4 |
| 5,683,429 A | 11/1997 | Mehra | | 602/14 |
| 5,697,953 A | 12/1997 | Kroll et al. | | 607/5 |
| 5,718,718 A | 2/1998 | Kroll et al. | | 607/5 |
| 5,800,469 A | 9/1998 | Nappholz | | 607/18 |
| 5,800,470 A | 9/1998 | Stein et al. | | 607/20 |
| 5,861,012 A | 1/1999 | Stroebel | | 607/28 |
| 5,978,704 A | 11/1999 | Ideker et al. | | 607/123 |
| 5,978,705 A | 11/1999 | KenKnight et al. | | 607/5 |
| 5,987,354 A | 11/1999 | Cooper et al. | | 607/5 |
| 6,002,962 A | 12/1999 | Huang et al. | | 607/5 |
| 6,006,131 A | 12/1999 | Cooper et al. | | 607/5 |
| 6,070,101 A * | 5/2000 | Struble et al. | | 607/9 |
| 6,148,230 A | 11/2000 | KenKnight | | 600/516 |
| 6,263,241 B1 * | 7/2001 | Rosborough et al. | | 607/6 |
| 6,275,730 B1 | 8/2001 | KenKnight et al. | | 607/5 |
| 6,285,907 B1 | 9/2001 | Kramer et al. | | 607/9 |
| 6,327,500 B1 | 12/2001 | Cooper et al. | | 607/5 |
| 6,772,005 B2 * | 8/2004 | Casavant et al. | | 607/4 |
| 2003/0009199 A1 * | 1/2003 | Reinke et al. | | 607/17 |
| 2004/0024421 A1 | 2/2004 | Ideker et al. | | |

FOREIGN PATENT DOCUMENTS

| | | |
|---|---|---|
| EP | 0554 208 A2 | 8/1993 |
| EP | 0 601 340 A1 | 6/1994 |
| EP | 0 653 223 A2 | 10/1994 |
| EP | 0804938 A2 | 11/1997 |
| WO | WO 93/20891 | 10/1993 |
| WO | WO 94/03334 | 2/1994 |
| WO | WO 94/12237 | 6/1994 |
| WO | WO96/23546 | 8/1996 |
| WO | WO 97/01373 | 1/1997 |
| WO | WO 98-53879 | 12/1998 |
| WO | WO99/65561 | 12/1999 |
| WO | WO 02/22207 | 3/2002 |
| WO | WO 02/051495 | 7/2002 |

OTHER PUBLICATIONS

Lammers, W. J.E.P. et al., *The use of fibrillation cycle length to determine spatial dispersion in electrophysiological properties and to characterize the underlying mechanism of fibrillation*, New Trends in Arrhythmias, vol. II, N.1, Jan.-Mar. 1986, pp. 109-112.

Laxer, Cary et al., *The Use of Computer Animation of Mapped Cardiac Potentials in Studying Electrical Conduction Properties of Arrhythmias*, IEEE, 1991, pp. 23-26.

Wolf, P. D. et al., *A 528 Channel System for the Acquisition and Display of Defibrillation and Electrocardiographic Potentials*, IEEE, 1993, pp. 125-128.

Allessie et al., "Regional control of atrial fibrillation by rapid pacing in concious dogs," *Circulation* 1991;84:1689-1697.

Capucci et al., "Capture window in human atrial fibrillation: evidence of an excitable gap," *J Cardiovasc Electrophysiol* 1999;10:319-327.

Cooper et al., "Internal Cardioversion of Atrial Fibrillation in Sheep," Atrial Fibrillation: Mechanisms and Therapeutic Strategies, pp. 325-332 (1994).

Cooper et al., "Internal Cardioversion of Atrial Fibrillation in Sheep," Circulation, vol. 87, No. 5, May 1993, pp. 1673-1685.

Daoud et al. "Response of Type I atrial fibrillation to atrial pacing in humans," Circulation 1996;94:1036-1040.

Feeser et al., "Strength-Duration and Probability of Success Curves for Defibrillation with Biphasic Waveforms," *Circulation*, vol. 82, No. 6, Dec. 1990, pp. 2128-2141.

Garcia-Calvo et al., "The effects of selective stellate ganglion manipulation on ventricular refractoriness and excitability," PACE, 1992;15:1492-1503.

Huang et al., "Evolution of the organization of epicardial activation patterns during ventricular fibrillation," J Cardiovasc Electrophysiol, 1998;9:1291-1304.

KenKnight et al., "Regional capture of fibrillating ventricular myocardium: Evidence of an excitable gap," Circ Res 1995;77:849-855.

Kirchhof et al., "Regional entrainment of atrial fibrillation studied by high-resolution mapping in open-chest dogs," Circulation 1993;88:736-749.

Knisley et al., "Line stimulation parallel to myofibers enhances regional uniformity of transmembrane voltage changes in rabbit hearts," Circ Res 1997;81:229-241.

Kroll, Mark W., "A Minimal Model of the Monophasic Defibrillation Pulse," PACE, vol. 16, Apr. 1993, Part 1, pp. 769-777.

Lewalter et al., "The Low Intensity Treadmill Exercise" Protocol for Appropriate Rate Adaptive Programming of Minute Ventilation Controlled Pacemakers, PACE, 18:1374-1387 (Jul. 1995).

(56) References Cited

OTHER PUBLICATIONS

Lok et al.; "Clinical Shock Tolerability and Effect of Different Right Atrial Electrode Locations on Efficacy of Low Energy Human Transvenous Atrial Defibrillation Using an Implantable Lead System", *JACC* 30:5 1324-1330 (1997).

Lüderitz et al., "Nonpharmacologic Strategies for Treating Atrial Fibrillation," The American Journal of Cardiology, vol. 77, Jan. 25, 1996, pp. 45A-52A.

Neri et al.; "Internal Cardioversion of Chronic Atrial Fibrillation in Patients", *PACE* 20 2237-2242 (1997).

Opthof et al., "Dispersion of refracteries in canine ventricular myocardium: Effects of sympathetic stimulation," Circ Res 1991;68:1204-1215.

Prof. Dr. med. Eckhard Alt; "Letters to the Editor", *PACE* 21 633-634 (1998).

Province et al., "Effect of pulse train amplitude and waveform on ability to entrain fibrillating rabbit ventricle with epicardial pacing," PACE, 22:A66 (1999) (Abstract).

Qin, Hao et al., "Recurrence Patterns After Failed Defibrillation of Spontaneous Ventricular Fibrillation During Acute Ischemia," Supplement to Journal of the American College of Cardiology, p. 3, Mar. 6, 2002, vol. 39, No. 5 Supplement A.

Qin, Hao et al., "Difibrillation Efficacy for Spontaneous and electrically-Induced Ventricular Fibrillation During Acute Ischemia," Supplement to Circulation Journal of the American Heart Association, #2125, 2000.

Qin, Hao et al., "Impact of Myocardial Ischemia and Reperfusion on Ventricular Defibrillation Patterns, Energy Requirements, and Detection of Recovery," (Circulation 2002;105:2537) Published online before print May 6, 2002, 10.1161/01.CIR.0000016702.86180.F6.

Rogers et al., "A quantitative framework for analyzing epicardial activation patterns during ventricular fibrillation," Ann Biomed Eng 1997; 25:749-760.

Rogers et al., "Recurrent wavefront morphologies: a method for quantifying the complexity of epicardial activation patterns," Ann Biomed Eng 1997; 25:761-768.

Rollins et al., "Macintosh based programmable cardiac stimulatr," J Am Coll Cardiol, 15:261A (1990) Abstract.

Vander et al. "*Human Physiology—The Mechanisms of Body Functio*," pp. 230-236, Jan. 1985.

Wharton et al., "Cardiac potential and potential gradient fields generated by single, combined, and sequential shocks during ventricular defibrillation," Circulation 1992; 85:1510-1523.

Wright et al., "Cardiac Rhythm Management Laboratory: In Vivo Study Protocol, Internal Atrial Defibrillation in Sheep Using Sequential Biphasic Waveforms," CRM Laboratory, University of Alabama—Birmingham Medical Center, Oct. 1995.

PCT International Search Report, International Application No. PCT/US01/47195 dated Jul. 23, 2002.

Office Action to Japanese Counterpart Application No. 2004-535983 dated Apr. 19, 2010.

* cited by examiner

POST-DEFIBRILLATION PACING METHODS AND DEVICES

FIELD OF THE INVENTION

The present invention is related to methods and apparatus for improving cardiac function in subjects.

BACKGROUND OF THE INVENTION

The heart is a muscular organ that is covered by a fibrous sac known as the pericardium. The space between the pericardium and the muscular organ is called the pericardial space. The walls of the heart are substantially formed from muscle (the myocardium) that differs from either skeletal or smooth muscle. The heart comprises atria and ventricles, each of which is composed of layers of myocardium that are formed to encase the blood-filled chambers. In operation, when the walls of a chamber contract, they come together similar to a squeezing fist. This contraction of the cardiac muscle is triggered by depolarization of the muscle membrane. To operate properly, the muscle contractions should be coordinated.

If the muscle contractions are not coordinated within the ventricles, blood may be sloshed back and forth within the ventricular cavities instead of being ejected into the aorta and pulmonary arteries. Thus, the complex muscle masses forming the ventricular pumps should contract substantially simultaneously for efficient pumping.

The heart is able to achieve this coordination because of (a) the tight junctions formed between adjacent cardiac fibers (the fibers are joined end to end at structures known as intercalated disks, which provide the points or junctions) which allow action potentials to be transmitted from one cardiac cell to another; and (b) the specialized muscle fibers in certain areas of the heart which provide the conducting system for proper excitation of the heart. The specialized fibers are in contact with fibers of the cardiac muscles to form gap junctions, which permit passage of action potentials from one cell to another. The specialized conduction system is configured, in normal operation, to provide a rapid and coordinated spread of excitation.

Cardiac muscle cells are autorhythmic, i.e., capable of spontaneous, rhythmical self-excitation. The sinoatrial (SA) node is the normal pacemaker for the entire heart or smooth muscle, and it is from this region that the excitation wave starts; it then moves or propagates through the remainder of the myocardium in a synchronized manner. The SA node region of the heart contains a small mass of specialized myocardial cells in the right atrial wall near the entrance of the superior vena cava that have a fast inherent rhythm, which allows the SA node to be the normal pacemaker. In unusual circumstances, other regions of the heart can become more excitable and provide a faster spontaneous rhythm. In this situation, this other region can become the pacemaker and the rhythm for the entire heart.

In normal operation, the cells of the SA node make contact with the surrounding atrial myocardium fibers. Thus, from the SA node, a wave of excitation spreads throughout the right atrium along the atrial myocardial cells via the gap junctions. In addition, the atrial tissue directs the impulse from the SA node directly to the left atrium, to simultaneously contract both atria.

The excitation wave then is distributed to the ventricles by way of a second small mass of specialized cells located at the base of the right atrium near the wall between the ventricles (the atrioventricular (AV) node). The AV node is configured to delay the propagation of action potentials (the wavefront) by about 0.1 second, to allow the atria to contract and empty the blood into the ventricle before ventricular contraction. The wavefront is then quickly dispersed along the specialized conducting fibers (down the interventricular septum to the ventricular free walls) and then through unspecialized (typical) myocardial fibers in the remaining myocardium.

The pumping of blood includes alternate periods of contraction and relaxation. The cardiac muscle has a relatively long refractory period (on the order of about 250 ms). This refractory period is a time during which the membrane is insensitive to stimulus (either totally unable to propagate an excitation wave or only able to do so upon exposure to an increased level of stimulation).

During ventricular fibrillation (VF) a number of independent activation wavefronts propagate simultaneously through the mycodardium. The propagation of these wavefronts may result in uncoordinated activity from the heart that may result in reduced or impaired cardiac function. Resuscitation attempts for cardiac arrest caused by VF include defibrillation shock. The defibrillation shock is intended to break up the propagation of the independent activation wavefronts to allow normal activation. Typically, defibrillation shock which does not result in the return of normal electrical and/or mechanical activity results in one of four potentially problematic outcomes. First, the defibrillation shock fails to halt the fibrillation. Second, the defibrillation shock halts the fibrillation but fibrillation re-occurs in the next few seconds or minutes. Third, the defibrillation shock may halt the fibrillation, but cardiac function does not progress on its own, i.e. asystole or absence of a heartbeat. Fourth, the defibrillation shock is successful and cardiac electrical activity returns after the shock but cardiac mechanical function is either absent or greatly reduced. This fourth condition may be referred to as pulseless electrical activity (PEA). Thus, improvements may be needed in the treatment of VF that may reduce the occurrence of one or more these problematic results. In particular, improvements may be needed to provide a reduction in the incidence of a return to fibrillation and/or of PEA.

SUMMARY OF THE INVENTION

Embodiments of the present invention provide methods, systems and computer program products for cardiac pacing in a patient. A defibrillation shock is applied to a heart of the patient and a pacing stimulation signal automatically applied to the heart of the patient subsequent to termination of the defibrillation shock. In certain embodiments of the present invention, the pacing stimulation may be applied to the heart of the patient within about two seconds or less of termination of the defibrillation shock. Furthermore, the pacing stimulation signal may be applied to the heart of the patient subsequent to termination of the defibrillation shock irrespective of a characterization of electrical activity detected in the heart. The defibrillation shock may be for VF, AF and/or other conditions.

In particular embodiments of the present invention, the pacing stimulation signal provides single pacing stimulation. In other embodiments, the pacing stimulation signal provides paired pacing stimulation. Cardiac activity may be detected and paired pacing stimulation selectively applied based on the detected cardiac activity. The detected cardiac activity may be associated with application of the single pacing stimulation. A signal specifying application of paired pacing could also be detected and paired pacing stimulation selectively applied based on the detected signal.

In yet further embodiments of the present invention, the defibrillation shock is applied to the heart of the patient using at least one first set of electrodes and the pacing stimulation signal is applied to the heart of the patient using at least one second set of electrodes. The first set of electrodes and the second set of electrodes may be the same or different sets of electrodes.

In other embodiments of the present invention, paired pacing stimulation is selectively applied to the heart based on receipt of an external specification and/or sensed variables associated with cardiac activity. The sensed variables associated with cardiac activity may include a pulse pressure below a predefined threshold, changes in impedance, changes in distance between electrodes, changes in the rate of change of distance between electrodes and/or detection of motion. The external specification may be operating instructions input from a healthcare provider.

In additional embodiments of the present invention, a cardiac pacing system includes a controller circuit configured to automatically apply a pacing stimulation signal to a heart of a patient immediately subsequent to termination of a defibrillation shock. The controller circuit may be further configured to apply the pacing stimulation within about two seconds or less of termination of the defibrillation shock. Additionally, the controller circuit may be configured to automatically apply the pacing stimulation irrespective of whether normal electrical activity is detected in the heart.

In particular embodiments of the present invention, the pacing controller is configured to provide single pacing stimulation. In other embodiments, the pacing controller is configured to provide paired pacing stimulation. The pacing controller may also be configured to detect cardiac activity and selectively apply paired pacing stimulation based on the detected cardiac activity. The detected cardiac activity may be associated with application of the single pacing stimulation. A signal specifying application of paired pacing could also be detected and paired pacing stimulation selectively applied based on the detected signal.

In still further embodiments of the present invention, the defibrillation shock is applied to a heart of a patient using at least one first set of electrodes and the controller circuit is further configured to apply the pacing stimulation signal to the heart of the patient subsequent to termination of the defibrillation shock using at least one second set of electrodes. The first set of electrodes and the second set of electrodes may be the same or different sets of electrodes. Electrodes may be at other locations within the body or external to the body such as by application to the skin.

The controller circuit may also be configured to selectively apply paired pacing stimulation to the heart based on at least one of receipt of an external specification and/or sensed variables associated with cardiac activity. The sensed variables associated with cardiac activity may be a pulse pressure below a predefined threshold. The external specification may be an instruction from a healthcare provider.

The controller circuit may be configured to be disposed within an implantable housing for implantation in the patient. The controller circuit could also be configured to be external to the patient.

In yet other embodiments of the present invention, the cardiac pacing system includes a defibrillator circuit configured to apply the defibrillation shock to the heart of the patient. The defibrillator circuit may be further configured to indicate termination of the defibrillation shock to the controller circuit. The defibrillator circuit and the controller circuit may be configured to be disposed within an implantable housing for implantation in the patient. The defibrillator circuit and the controller circuit may also be disposed in separate devices. For example, one of the defibrillator circuit and the controller circuit may be configured to be disposed within an implantable housing and the other of the defibrillator circuit and the controller circuit may be configured to be external to the patient.

A cardiac pacing system according to further embodiments of the present invention may also include at least one set of electrodes for application of the pacing stimulation signal to the heart of the patient.

In further embodiments of the present invention, the cardiac pacing system detects cardiac activity and/or function of the heart and selects a type of pacing stimulation to apply to the heart of the patient subsequent to termination of the defibrillation shock based on the detected cardiac activity and/or function. The selected type of pacing may be automatically applied to the patient's heart. The cardiac pacing system may detect the cardiac activity and/or function before or after applying the defibrillation shock to a heart of the patient. The selected type of pacing stimulation may include single pacing stimulation, paired pacing stimulation and/or a combination of the two.

In still further embodiments of the present invention, the cardiac pacing system inhibits application of the pacing stimulation based on the detection of cardiac activity. The detected cardiac activity may include at least one of blood pressure and/or spontaneous electrical activity.

As will be appreciated by those of skill in the art in light of the present disclosure, the present invention may be embodied as systems, methods and/or computer program products.

DESCRIPTION OF EMBODIMENTS OF THE INVENTION

Figure 1:
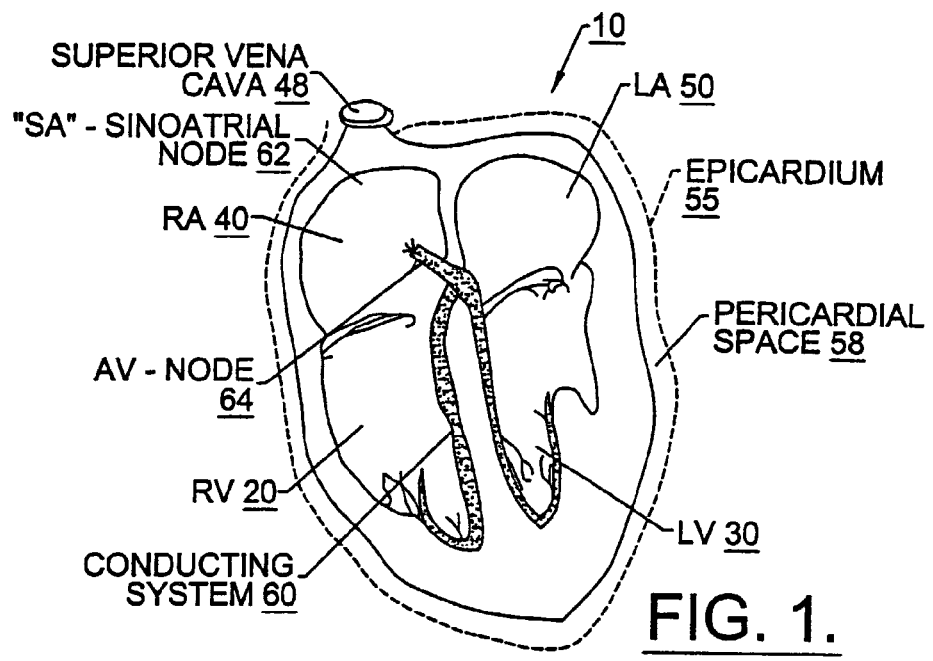
FIG. 1 is a schematic illustration of a human heart.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain features, elements and/or components may be exaggerated for clarity.

The present invention may be used for pacing the heart after application of a defibrillation shock. Subjects according to the present invention can be any animal subject, are preferably mammalian subjects (e.g., humans, canines, felines, bovines, caprines, ovines, equines, rodents, porcines, and/or lagomorphs), and more preferably are human subjects.

Embodiments of the present invention provide for the automatic application of a pacing stimulation upon termination of a defibrillation shock. As used herein, "automatic" and "automatically" refer to providing the pacing stimulation irrespective of detected heart activity such that the shock may be applied irrespective of whether success or failure of the defibrillation shock is detected or whether the heart has returned to a pre-shock normalcy. The defibrillation shock may be a ventricular fibrillation shock and/or an atrial fibrillation shock. Pacing stimulation may be applied through some or all of the same electrode(s) that provide the defibrillation shock or may be applied through different electrodes. Furthermore, the pacing may be single and/or paired pacing.

One or more sets of electrodes may be placed at one or more sites. References to an electrode herein may refer to one or more electrodes associated with a stimulation site. Accordingly, references to stimulation of an electrode or application of a stimulation signal may refer to stimulation of the one or more electrodes associated with a stimulation site or path. The various stimulation sites utilized may depend on the particular patient and/or pacing regime. Such sites may, for example, include those described in U.S. Pat. Nos. 4,929,688 and 6,285,907, the disclosures of which are incorporated herein by reference as if set forth fully herein. Similarly, differing electrode configurations and locations may also be utilized with embodiments of the present invention. For example, the placement and type of electrodes may be as described in U.S. patent application Ser. No. 09/742,651 filed Dec. 21, 2000 and entitled "PACING METHODS AND DEVICES FOR TREATING CARDIAC ARRHYTHMIAS AND FIBRILLATION," the disclosure of which is incorporated herein by reference as if set forth in its entirety. Suitable commercially available electrodes may include defibrillation and/or pacing electrodes well known to those of skill in the art. In some embodiments, the electrodes that are adapted to reside in the heart in the vein(s) of a subject may be particularly suitable. See also, U.S. Pat. Nos. 5,107,834, 5,224,476, 5,978,704, and 6,002,962, the contents of which are hereby incorporated by reference as if recited in full herein.

The catheters or electrodes may also include sensors for measuring cardiac function. For example, a catheter may include one or more stimulation electrodes and/or sensors for sensing one or more of the onset of a treatment condition or the intrinsic cardiac cycle. See U.S. Pat. No. 5,978,704, entitled, Method and Apparatus for Treating Cardiac Arrhythmia, the contents of which are hereby incorporated by reference as if recited in full herein. Furthermore, according to embodiments of the present invention, the sensors may also include sensors for detecting indicators of cardiac function, such as, for example, measuring changes in impedance, changes in distance between electrodes and/or the rate of change of distance and/or detection of motion through, for example, use of an accelerometer. As used herein, motion refers to acceleration, velocity, displacement, integrals of acceleration, displacement and/or velocity and/or derivatives of acceleration, displacement and/or velocity. Furthermore, detection of cardiac function and/or characteristics may be carried out as described in concurrently filed and commonly assigned U.S. patent application Ser. No. 10/238,342 entitled "METHODS, SYSTEMS AND COMPUTER PROGRAM PRODUCTS FOR TREATING FIBRILLATION IN A PATIENT BASED ON THE PRESENCE OF FIBRILLATION FOLLOWING ADMINISTRATION OF DEFIBRILLATION THERAPY," or as described in U.S. patent application Ser. No. 10/238,340 entitled "DEVICES FOR DETECTING THE PRESENCE OF CARDIAC ACTIVITY FOLLOWING ADMINISTRATION OF DEFIBRILLATION THERAPY," the disclosures of which are incorporated herein as if set forth in their entirety.

Figure 2:
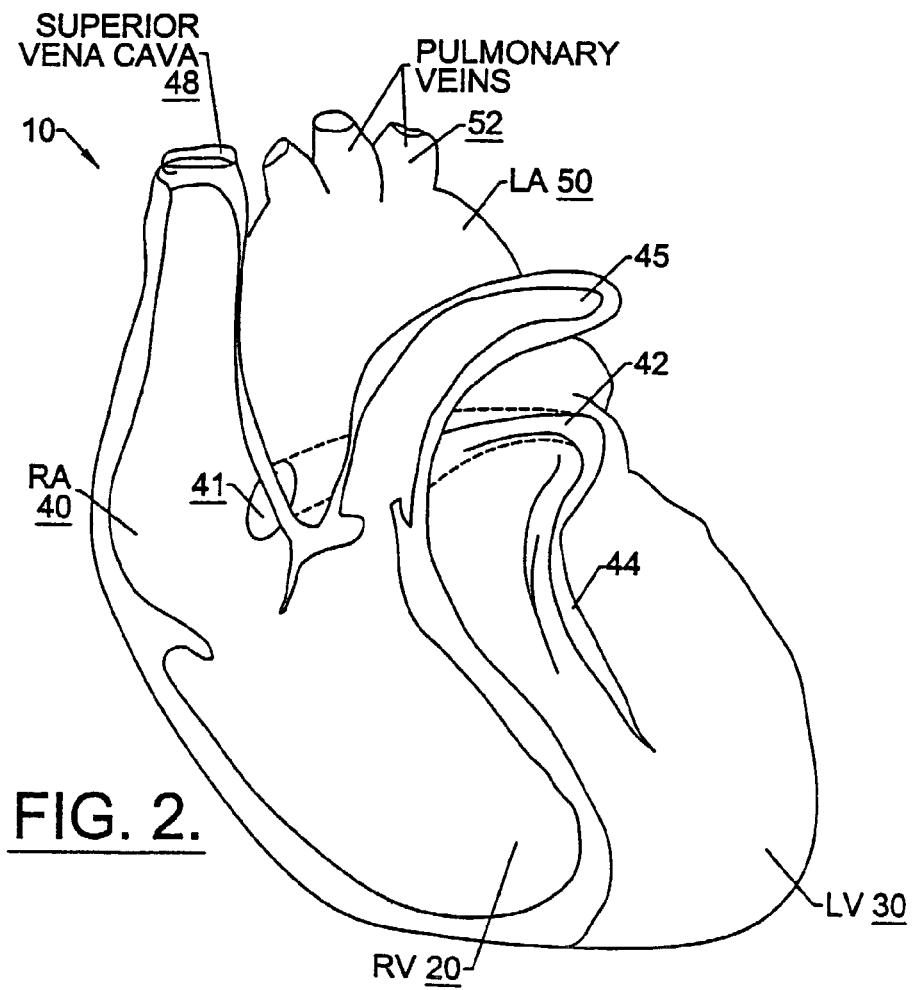
FIG. 2 is a schematic illustration of a human heart.

Anatomically, the heart includes a fibrous skeleton, valves, the trunks of the aorta, the pulmonary artery, and the muscle masses (myocardium) of the cardiac chambers (i.e., right and left atria and right and left ventricles). The schematically illustrated portions of the heart 10 shown in one or more of FIGS. 1 or 2 include the right ventricle "RV" 20, the left ventricle "LV" 30, the right atrium "RA" 40 (the term "right atrium" herein including the superior vena cava and innominate vein), the left atrium "LA" 50 (and parts thereof), the superior vena cava 48, the coronary sinus "CS" 42, the great cardiac vein 44, the left pulmonary artery 45 (the term "left pulmonary artery" herein includes the main pulmonary artery and the right ventricular outflow tract), and the coronary sinus ostium or "OS" 41. FIG. 1 also illustrates the epicardium 55 (shown in dotted line) surrounding the walls of the heart (i.e., the myocardium) and the pericardial space 58 therebetween. FIG. 2 also illustrates the pulmonary veins 52 and neighboring regions. Other regions of interest may include the atrial septum, right and left atrial appendages, and the tricuspid annulus. FIG. 1 also illustrates the conducting system 60, the SA node 62 and the AV node 64.

As mentioned above, the desired sites or localized region(s) selected for placement of the electrodes, the stimulation sites, defibrillation and/or pacing the heart according to embodiments of the present invention may vary depending on the physiology or ailment of the patient and/or the particular selected pacing protocol employed. As such, the electrodes may be positioned in a number of regions, internal and/or external to the body, and by a number of different techniques so that they are proximate to and/or in contact with the desired localized region of the myocardium or other sites of interest. For example, electrodes may be placed directly on the surface of the patient's chest. By way of further example, one or more electrodes can be positioned in the natural lumens of the heart (atriums, ventricles, veins, arteries, etc.), or in the pericardial space, on the outer, inner surfaces of the cardiac walls, or within the thickness of the muscle walls. The electrodes may be positioned into the body of the subject by surgical techniques or by inserting them using locating catheters holding same, and the like. In some embodiments, certain electrodes are configured and sized such that each is able to contact the tissue at a respective stimulation or sensing site during the heartbeats. As used herein, "localized" refers to the electrical stimuli being delivered to a portion of the heart rather than to the entire heart.

Thus, as noted above, the pacing electrodes may be positioned in the pericardial space or other localized regions of the heart. For example, the pacing electrode(s) can be held on a catheter and inserted into the endocardium or threaded through the heart and inserted into the veins in the heart (threaded through the OS and looped into the veins). In some embodiments, pacing of the left atrium may be performed by locating an electrode(s) to extend in a portion of the left atrium and into the pulmonary veins to help eradicate or control fibrillation activation in this region. Locating one or more electrodes in the pulmonary vein may be particularly suitable for the treatment of atrial fibrillation. Other exemplary placements are discussed below.

As described above, the driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers then travels into the atria and subsequently passing through the AV node and, after a slight delay, into the ventricles. Sensing cardiac activation or contractions while pacing can provide data to the pacing system (controller or cardiac monitor) which can be assessed to determine and adjust, as needed, a number of operational parameters such as, for example: (a) when to stop the pacing stimulation; (b) the speed or rate of the pacing stimulation (increase or decrease the pacing rate), the duration or intensity of the stimulation pulse(s); (c) whether the tissue is being successfully captured; and (d) the number of pulses/pulse trains to be relayed to the localized region.

According to embodiments of the present invention, pacing is applied to the heart automatically after application of a defibrillation shock. As used herein, "pacing" may include stimulation having any cycle length or combination of cycle lengths. For example, pacing may include single pacing, paired pacing or any combination of the two. The pacing stimulation may be provided to reduce the likelihood of redevelopment of arrhythmia and/or to improve mechanical function of the heart. Furthermore, the timing of pacing stimulation may be controlled by feedback such as described in U.S. patent application Ser. No. 10/210,587 filed Jul. 31, 2002 and entitled "Pacing Methods and Devices Using Feedback Controlled Timing," the disclosure of which is incorporated herein by reference as if set forth fully herein.

Figure 3:
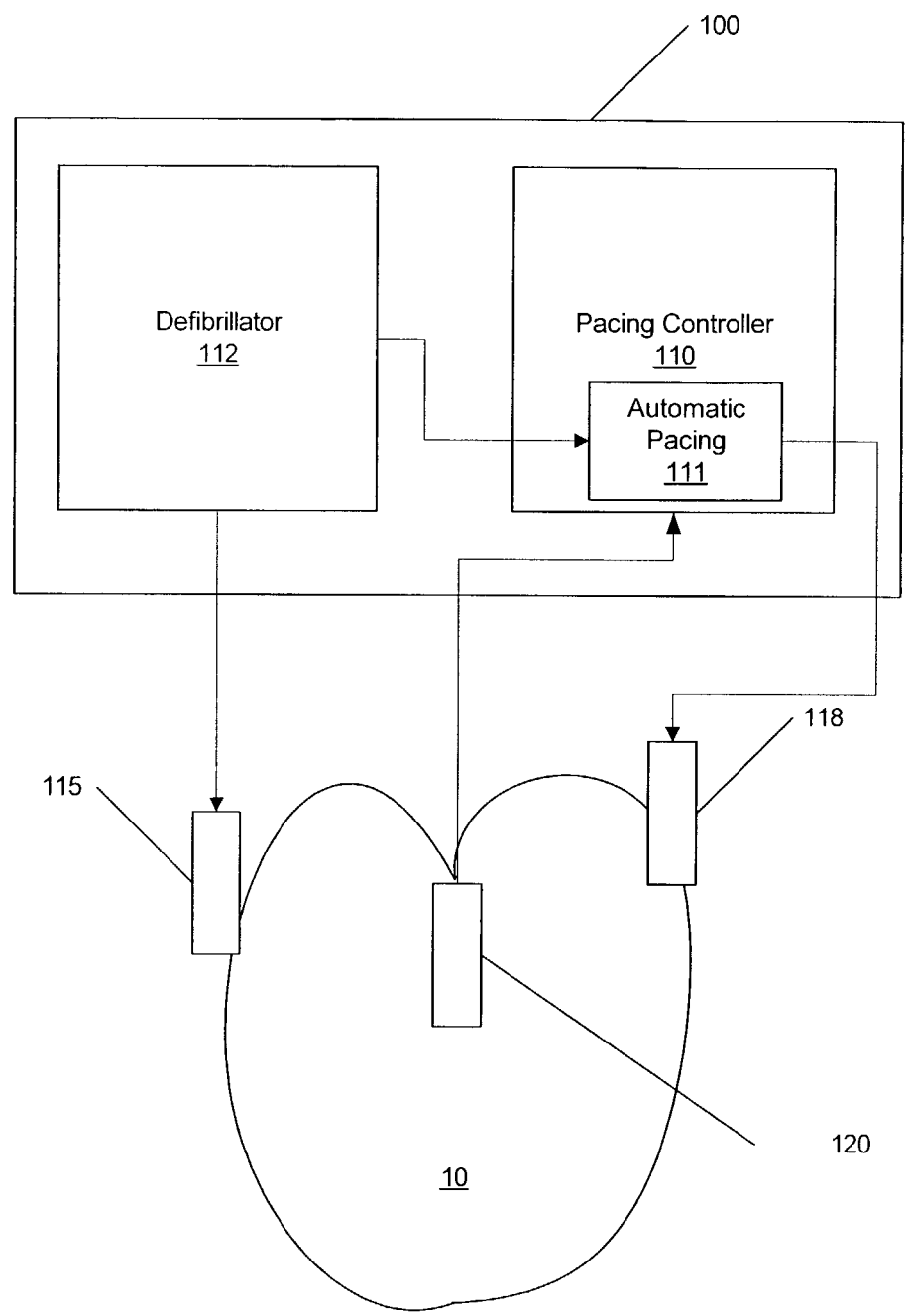
FIG. 3 is a block diagram illustrating embodiments of the present invention.

A system for providing automatic application of pacing according to certain embodiments of the present invention is illustrated in FIG. 3. As seen in FIG. 3, a defibrillation/pacing system 100 according to certain embodiments of the present invention includes a pacing controller circuit 110 and a defibrillator circuit 112. The pacing controller circuit 110 and defibrillator circuit 112 have one or more sets of electrodes 115 and 118 that are placed in particular locations or regions of the heart 10 as discussed above (the sites shown are by way of example only). The particular location may depend on the particular application for defibrillation and/or pacing. Such locations will be apparent to those of skill in the art in light of the above disclosure and will, therefore, not be described further herein. As described above, the same electrodes may be utilized for defibrillation as are used for pacing. Alternatively, different ones or sets of electrodes may be used for defibrillation as are used for pacing. Finally, combinations of common and different electrodes may be used for defibrillation and pacing. As shown in FIG. 3, a sensor 120 may also be provided to sense cardiac function such that the pacing controller circuit 110 may control application of pacing stimulation as described herein. Furthermore, the pacing controller circuit 110 may receive external inputs, for example, from a healthcare provider, to further control the application of pacing as discussed below. The pacing controller circuit 110 includes an automatic pacing circuit 111 that automatically applies pacing stimulation after a defibrillation shock.

The pacing controller circuit 110 and/or defibrillator circuit 112 may be provided as part of an external device (such as a remote housing which holds the operating components therein), or may be configured to be disposed in a single or dual biocompatible implantable housing(s) that holds the operating circuitry in a hermetically sealed body. Similarly, one of the pacing controller circuit 110 or the defibrillator circuit 112 could be incorporated in an external device while the other of the pacing controller circuit 110 and the defibrillator circuit 112 be disposed in an implantable housing for implantation in a patient. The pacing controller 110 and/or defibrillator circuit 112 can include an electronic circuit that includes one or more amplifiers (not shown) for amplifying sensed cardiac signals and/or for providing stimulation to the electrodes 115 and/or 118. The pacing controller 110 and/or defibrillator circuit 112 may also include conventional circuitry to analyze the amplified signals to detect the onset or presence of an atrial and/or ventricular arrhythmia or fibrillation condition and to identify when or if ventricular fibrillation (or other arrhythmia, depending on the specific treatment for which the device is configured) is present. Furthermore, the defibrillator circuit 112 may be a conventional defibrillator circuit. However, as described in further detail below, in certain embodiments of the present invention the defibrillator circuit 112 provides a signal to the pacing controller circuit 110 that is provided to the automatic pacing circuit 111 or the automatic pacing circuit 111 monitors the operation of the defibrillator circuit 112 from which the automatic pacing circuit 111 may determine when a defibrillation shock has terminated.

In certain embodiments, the pacing controller 110 and/or defibrillator circuit 112 can be used to time a defibrillation shock pulse to reduce the likelihood that associated defibrillation shock pulses are delivered during sensitive portions of the cardiac cycle so as to reduce the possibility of inducing ventricular fibrillation. Ventricular sensing for timing the shocks for atrial defibrillation may be performed from the RV and/or LV electrodes used as in defibrillation devices known to those of skill in the art. See U.S. Pat. No. 5,978,704, the contents of which were incorporated by reference hereinabove.

In operation, according to certain embodiments of the present invention, the defibrillator circuit 112 applies a defibrillation shock to the heart 10 through the electrode(s) 115. The defibrillator circuit 112 notifies the pacing controller circuit 110 when the defibrillation shock has terminated and the automatic pacing circuit 111 automatically applies pacing stimulation to the heart 10 through the electrode(s) 118. Alternatively, the pacing controller circuit 110 could sense the termination of the defibrillation shock, be notified of the initiation of the shock and wait a predefined time period or utilize other similar techniques to determine that the defibrillation shock has terminated. The pacing controller circuit 110 may also sense cardiac function utilizing the sensor 120 so as to control the timing of or operative application of the pacing stimulation as described herein. If sensing of cardiac function is performed immediately after the application of the defibrillator shock, such sensing may be carried out be disconnecting sensor leads from sensing circuitry during application of the defibrillator pulse, for example, through the use of a relay. Systems and operations for sensing cardiac function/characteristics immediately after application of a defibrillator pulse are described in U.S. patent application Ser. No. 10/238,340 which has been incorporated herein by reference as if set forth in its entirety.

While embodiments of the present invention are described herein with reference to the particular division of function and/or architecture illustrated in FIG. 3, as will be appreciated by those of skill in the art in light of the present disclosure, other division of functions and/or architectures may be utilized while still benefiting from the teachings of the present invention. For example, the defibrillator circuit 112 and the pacing controller circuit 110 may be separate devices or may be a single device. Furthermore, the pacing controller circuit 110 may be incorporated into the defibrillator circuit 112. Thus, the architecture illustrated in FIG. 3 is provided for illustrative purposes only and should not be construed as limiting the scope of the present invention.

Figure 4:
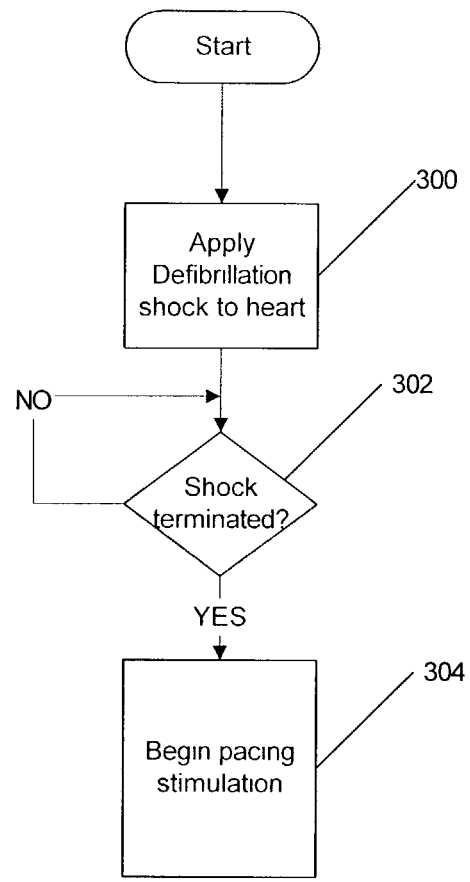
FIG. 4 is a flowchart illustrating operations according to embodiments of the present invention.

FIG. 4 is a flowchart illustrating operations according to embodiments of the present invention. As seen in FIG. 4, a defibrillation shock is applied to the heart 10 (block 300), for example, by the defibrillator circuit 112. Termination of the defibrillation shock is determined (block 302), for example, by the defibrillator circuit 112 notifying the pacing controller circuit 110 of termination of the shock, the pacing controller circuit 110 detecting termination of the shock or the pacing controller circuit 110 waiting a sufficient time to assure that the defibrillation shock has terminated. After termination of the defibrillation shock (block 302), pacing stimulation is automatically applied to the heart 10 (block 304) by, for example, the automatic pacing circuit 111. Thus, the application of the pacing stimulation may be carried out automatically irrespective of whether normal heart function has been detected or whether normal electrical activity has been detected in the heart.

According to certain embodiments of the present invention, the pacing stimulation is applied immediately after the defibrillation shock has been terminated. As used herein, the term "immediately" refers to application of the pacing stimulation before a conventional electro-cardiagram can detect cardiac activity to determine if the defibrillation shock successfully halted fibrillation. Thus, for example, application of the pacing stimulation carried out in less than about 2 to 4 seconds after the termination of the defibrillation shock may be considered immediately after termination of the defibrillation shock. In particular embodiments of the present invention, the pacing stimulation is applied within about 2 seconds or less of termination of the defibrillation shock, in further embodiments the pacing stimulation is applied within about 1 second or less of the termination of the defibrillation shock, and in still further embodiments of the present invention, the pacing stimulation is applied within about 0.5 seconds or less of the termination of the defibrillation shock.

As briefly described above, the pacing stimulation may be single pacing and/or paired pacing. For single pacing, the pacing stimulation may be applied utilizing conventional timing relationships. Furthermore, conventional paired pacing may also be utilized according to certain embodiments of the present invention. For example, the timing between each pair of stimulation pulses may be constant and the timing between pulses within a pair may be constant. The pacing rate for single and/or paired pacing may be predefined or may be based on sensed variable, including cardiac electrical activity before or after the defibrillation shock as is known to those of skill in the art. The strength of the pacing stimulus may be predefined or may be dynamically established utilizing auto-capture techniques known to those of skill in the art. Paired pacing could also be selectively utilized based on operator specification and/or sensed variables, such as pulse pressure lower than a predefined value, heat rate, timing and/or morphology of at least one intrinsic ventricular beat, changes in impedance, changes in distance and/or displacement and/or the rate of change of distance between two locations, and/or motion of a location associated with the heart. Electrode locations as described above may be utilized for single and/or paired pacing.

Figure 5:
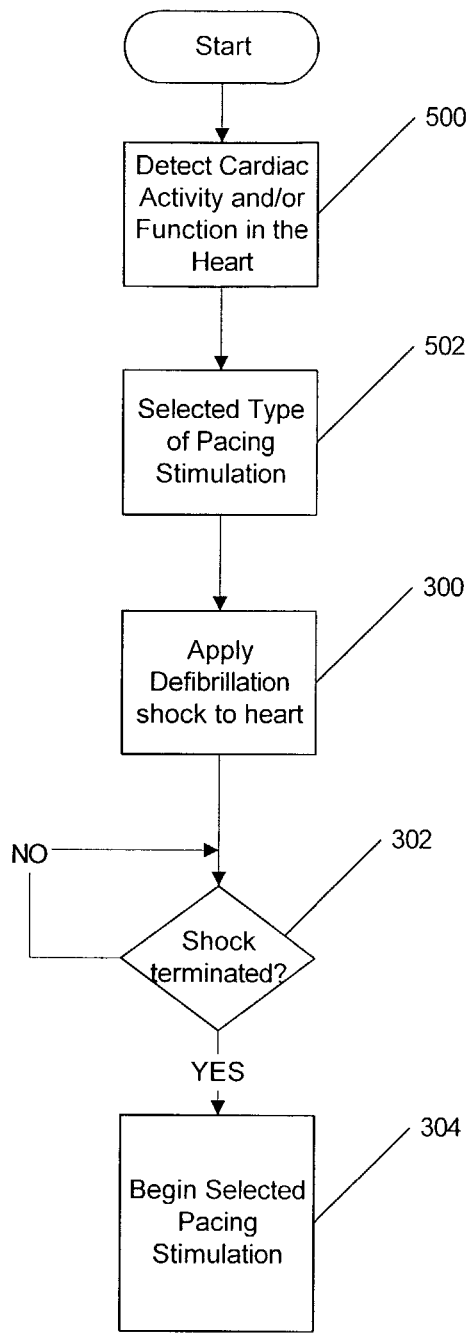
FIG. 5 is a flowchart illustrating operations according to further embodiments of the present invention.

FIG. 5 is a flowchart illustrating operations according to further embodiments of the present invention. As seen in FIG. 5, cardiac activity and/or function is detected in the heart (block 500). Although the detection of cardiac activity and/or function is illustrated as occurring before application of the defibrillation shock in FIG. 5, the present invention is not limited to this configuration. For example, cardiac activity may be detected after the application of the defibrillation shock without departing from the teachings of the present invention. A type of pacing stimulation is selected based on the detected cardiac activity and/or function (block 502). For example, a series of detected electrical signals (cardiac activity) may indicate that the patient would not respond to single pacing stimulation, therefore, paired pacing stimulation may be selected for this patient based upon the electrical signals. Similarly, a low pulse pressure may indicate impaired cardiac function, which may be improved by paired pacing. The type of pacing stimulation selected may include single pacing stimulation, paired pacing stimulation and/or a combination of the two.

The defibrillation shock is applied to the heart 10 (block 300), for example, by the defibrillator circuit 112. Termination of the defibrillation shock is determined (block 302), for example, by the defibrillator circuit 112 notifying the pacing controller circuit 110 of termination of the shock, the pacing controller circuit 110 detecting termination of the shock or the pacing controller circuit 110 waiting a sufficient time to assure that the defibrillation shock has terminated. After termination of the defibrillation shock (block 302), the selected pacing stimulation (block 502) is automatically applied to the heart 10 (block 304) by, for example, the automatic pacing circuit 111.

Figure 6:
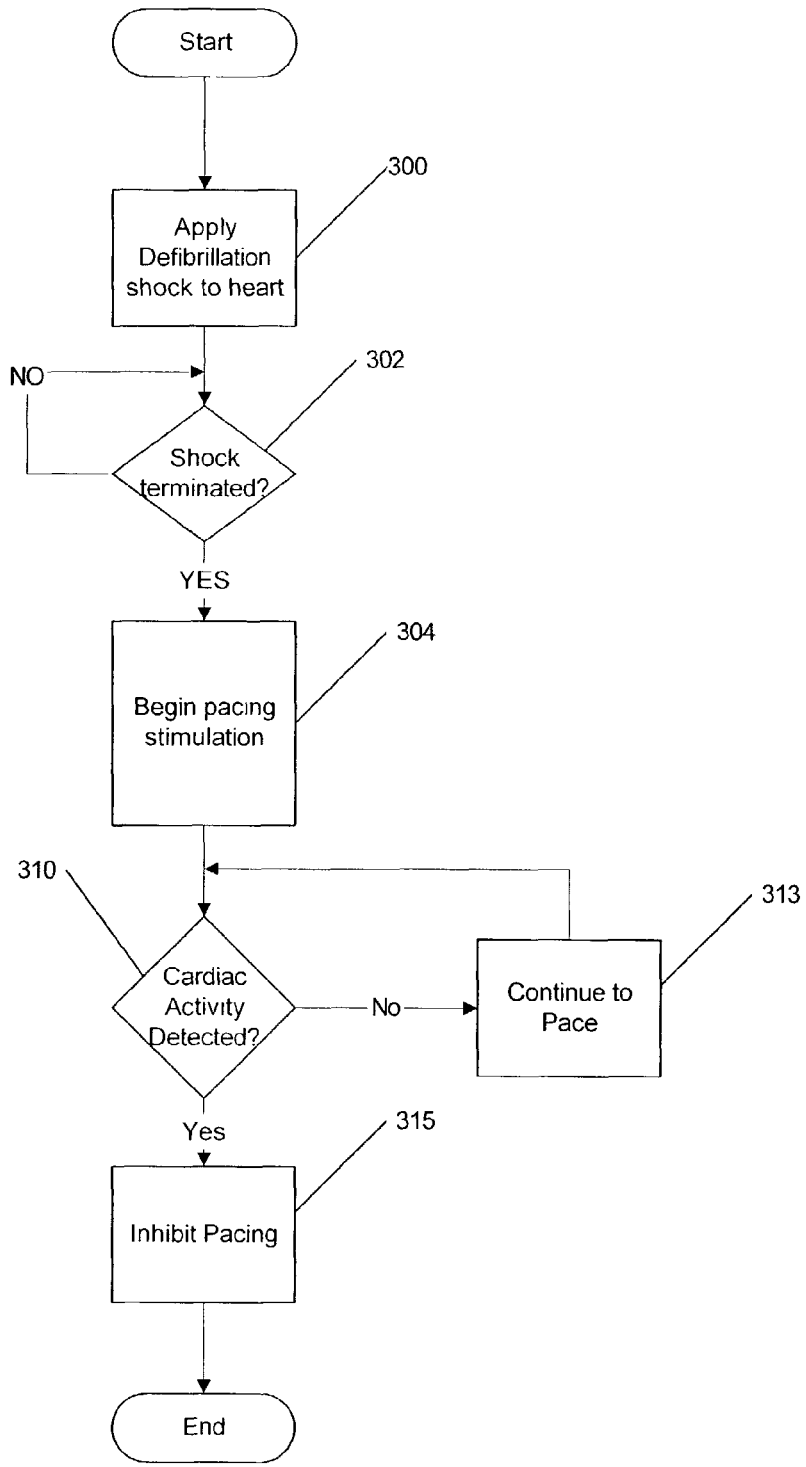
FIG. 6 is a flowchart illustrating operations according to further embodiments of the present invention.

FIG. 6 is a flowchart illustrating operations according to further embodiments of the present invention. As seen in FIG. 6, after initiation of application of the defibrillation shock (block 300) and termination of the defibrillation shock (block 302) as described above with reference to FIG. 4, a pacing stimulation signal is applied to the heart 10 (block 304). Still referring to FIG. 6, it is determined if cardiac activity is present (block 310). Cardiac activity may be detected by detecting, for example, blood pressure, spontaneous electrical activity or the like. If it is determined that cardiac activity is present (block 310), pacing is inhibited (block 315). Pacing may be inhibited by, for example, halting pacing and/or pacing less frequently. If, on the other hand, it is determined that cardiac activity is not present (block 310), pacing continues uninterrupted (block 313).

Figure 7:
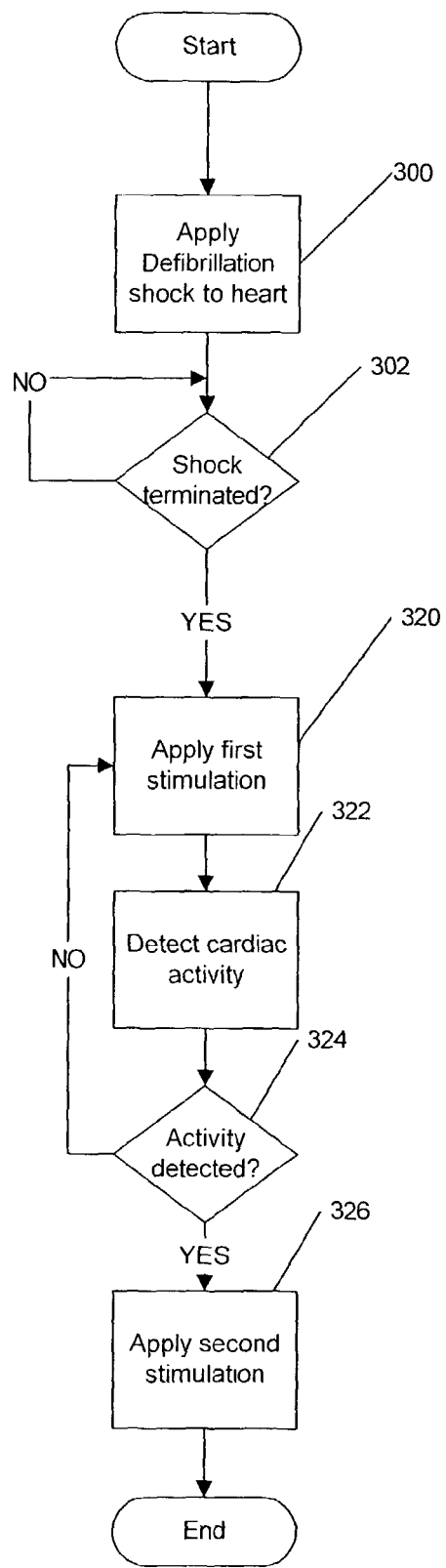
FIG. 7 is a flowchart illustrating operations according to further embodiments of the present invention.

Further embodiments of the present invention utilizing paired pacing are also illustrated in FIG. 7. As illustrated in FIG. 7, after initiation of application of the defibrillation shock (block 300) and termination of the defibrillation shock (block 302) as described above with reference to FIG. 4, a first pacing stimulation signal is applied to the heart 10 (block 320). Still referring to FIG. 7, activity of the heart is detected that results from the application of the first pacing stimulation signal (block 322). Based on detected cardiac activity associated with or responsive to the application of the first stimulation signal (block 324), a second stimulation signal is selectively applied to the heart 10 (block 326) so as to selectively provide paired pacing based on the detected cardiac activity. The selective application of the second stimulation signal to provide paired pacing may be based on the nature of the sensed cardiac activity. Thus, if the detected cardiac activity is indicative of low cardiac function, the second stimulation signal may be applied so as to provide paired pacing to improve mechanical function of the heart. For example, the sensed cardiac function may include sensing low pulse pressure impedance signals, heat rate, timing and/or morphology of at least one intrinsic ventricular beat, changes in impedance, changes in distance and/or displacement and/or the rate of change of distance between two locations, and/or motion of a location associated with the heart. Thus, according to the embodiments illustrated in FIG. 7, the second stimulus is provided to provide paired pacing based on cardiac activity corresponding to the first stimulus (single pacing).

In further embodiments of the present invention, paired pacing may be initiated by receipt of a signal from an external source, such as a healthcare professional, that may be utilized to selectively activate paired pacing. In such a case, the operations of FIG. 7 could be modified by modifying block 322 to determine if the signal from the external source is detected. If so, the second stimulation of block 326 would be provided. In an implantable device, the signal from an external source may be a radio frequency signal or other such technique for communicating with an implantable device. Similarly, a software switch may be set to provide the signal from an external source. In an external device, a switch setting (either hardware or software) may be utilized to select between single pacing and paired pacing.

In still further embodiments of the present invention, the detected cardiac activity need not be responsive to the application of the first stimulation signal. In such embodiments, FIG. 7 could be modified such that activity of the heart is detected irrespective of whether the activity results from application of the first stimulation signal (block 322). Based on the detected cardiac activity (block 324), a second stimulation signal is selectively applied to the heart 10 (block 326) so as to selectively provide paired pacing based on the detected cardiac activity.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects, all generally referred to herein as a "circuit." Furthermore, the present invention may take the form of a computer program product on a computer-usable storage medium having computer-usable program code means embodied in the medium. Any suitable computer readable medium may be utilized including, a memory device, hard disks, CD-ROMs, optical storage devices, a transmission media, such as a wireless transmission media and/or those supporting the Internet or an intranet, or magnetic storage devices.

The present invention is described herein with reference to flowchart illustrations and/or block and/or flow diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart and/or block and/or flow diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

While embodiments of the present invention have been described with reference to a particular architecture and/or division of functions, the present invention should not be construed as limited to such architecture and/or division. Thus, other architectures and/or division of functions capable of carrying out the operations described herein may be utilized while still falling within the teachings of the present invention. Furthermore, while embodiments of the present invention have been described with reference to particular circuits, such circuits may include discrete components, processors, such as a microprocessor and/or signal processor, analog circuits, digital circuits and/or combinations thereof. Furthermore, embodiments of the present invention may be provided as an entirely hardware embodiment, an entirely software embodiment or combinations of hardware and software.

With regard to the operations illustrated in the flowcharts described above, as will be appreciated by those of skill in the art in light of the present disclosure, embodiments of the present invention are not limited to the specific sequence or sequences of operations described therein. Thus, for example, operations in the flowcharts may be provided out of sequence or concurrently. Similarly, other sequences of operations may be utilized while still providing the feedback adjustment according to embodiments of the present invention. Accordingly, the present invention should not be construed as limited to the particular operations or sequence of operations illustrated in the flowcharts.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of cardiac pacing in a patient, comprising:
applying a defibrillation shock to a heart of the patient;
automatically applying a pacing stimulation signal to the heart of the patient subsequent to termination of the defibrillation shock, wherein the pacing stimulation signal comprises single pacing stimulation and is applied by activating one or more electrodes of a first set of electrodes;
detecting cardiac activity associated with application of the single pacing stimulation; and
selectively applying paired pacing stimulation based on the detected cardiac activity by activating one or more electrodes of the first set of electrodes, wherein the single pacing stimulation comprises a first timing relationship between single pacing pulses and the second pacing stimulation comprises a paired timing relationship between pairs of pacing pulses, and the one or more electrodes of the first set of electrodes activated to apply the pacing stimulation consist only of the same one or more electrodes activated to selectively apply paired pacing stimulation.

2. The method of claim 1, wherein the step of automatically applying a pacing stimulation comprises applying a pacing stimulation signal to the heart of the patient within about two seconds of termination of the defibrillation shock.

3. The method of claim 1, wherein the step of automatically applying a pacing stimulation comprises applying a pacing stimulation signal to the heart of the patient subsequent to termination of the defibrillation shock irrespective of a characterization of electrical activity detected in the heart.

4. The method of claim 1, wherein the step of applying a defibrillation shock to a heart of the patient comprises applying a defibrillation shock to a heart of a patient using at least one first set of electrodes;
wherein the step of automatically applying a pacing stimulation signal comprises automatically applying a pacing stimulation signal to the heart of the patient subsequent to termination of the defibrillation shock using at least one second set of electrodes; and
wherein the first set of electrodes and the second set of electrodes are different sets of electrodes.

5. The method of claim 1, wherein the step of applying a defibrillation shock to a heart of the patient comprises applying a defibrillation shock to a heart of a patient using at least one first set of electrodes;
wherein the step of automatically applying a pacing stimulation signal comprises automatically applying a pacing stimulation signal to the heart of the patient subsequent to application of the defibrillation shock using at least one second set of electrodes; and
wherein the first set of electrodes and the second set of electrodes are a same set of electrodes.

6. The method of claim 1, wherein selectively applying further comprises selectively applying paired pacing stimulation to the heart based on at least one of receipt of an external specification and sensed variables associated with cardiac activity.

7. The method of claim 6, wherein the sensed variables associated with cardiac activity comprise a pulse pressure below a predefined threshold, changes in impedance, changes in distance between electrodes, changes in the rate of change of distance between electrodes and/or detection of motion.

8. The method of claim 6, wherein the external specification comprises instruction from a healthcare provider.

9. The method of claim 1, wherein at least one of the defibrillation shock and the pacing stimulation are applied by an implantable device.

10. The method of claim 1, further comprising inhibiting application of the pacing stimulation if cardiac activity is detected.

11. The method of claim 10, wherein the detected cardiac activity comprises a detected blood pressure.

12. The method of claim 10, wherein the detected cardiac activity comprises spontaneous electrical activity.

13. A method of cardiac pacing in a patient, comprising:
applying a defibrillation shock to a heart of the patient;
automatically applying a pacing stimulation signal to the heart of the patient subsequent to termination of the defibrillation shock by activating one or more electrodes of a first set of electrodes;
detecting cardiac activity and/or function of the heart; and
selecting a type of pacing stimulation to apply to the heart of the patient subsequent to termination of the defibrillation shock based on the detected cardiac activity and/or function by activating one or more electrodes of the first set of electrodes, and wherein the step of automatically applying comprises automatically applying the selected type of pacing, wherein the type of pacing includes a single pacing stimulation comprising a first timing relationship between single pacing pulses and/or or a paired pacing stimulation comprising a second timing relationship between pairs of pacing pulses, and the one or more electrodes of the first set of electrodes activated to apply the pacing stimulation consist only of the same one or more electrodes activated to selectively apply paired pacing stimulation.

14. The method of claim 13, wherein detecting cardiac activity and/or function comprises detecting the cardiac activity and/or function before applying a defibrillation shock to a heart of the patient.

15. The method of claim 13, wherein detecting cardiac activity and/or function comprises detecting the cardiac activity and/or function after applying a defibrillation shock to a heart of the patient.

16. The method of claim 13, wherein the selected type of pacing stimulation comprises a combination of single pacing stimulation and paired pacing stimulation.

17. A cardiac pacing device, comprising: a defibrillator circuit configured to apply a defibrillation shock to the heart of a patient;
a controller circuit configured to automatically apply a pacing stimulation signal to a heart of a patient immediately subsequent to termination of the defibrillation shock by activating one or more electrodes of a first set of electrodes, wherein the pacing stimulation signal comprises single pacing stimulation and wherein the controller circuit is further configured to detect cardiac activity of the heart associated with application of the single pacing stimulation and selectively apply paired pacing stimulation based on the detected cardiac activity by activating one or more electrodes of the first set of electrodes, wherein the single pacing stimulation comprises a first timing relationship between single pacing pulses and the second pacing stimulation comprises a paired timing relationship between pairs of pacing pulses, and the one or more electrodes of the first set of electrodes activated to apply the pacing stimulation consist only of the same one or more electrodes activated to selectively apply paired pacing stimulation.

18. The cardiac pacing device of claim 17, wherein the controller circuit is further configured to apply the pacing stimulation within about two seconds of termination of the defibrillation shock.

19. The cardiac pacing device of claim 17, wherein the controller circuit is further configured to automatically apply the pacing stimulation irrespective of a characterization of electrical activity detected in the heart.

20. The cardiac pacing device of claim 17, wherein the defibrillation shock is applied to a heart of a patient using at least one first set of electrodes and wherein the controller circuit is further configured to apply the pacing stimulation signal to the heart of the patient subsequent to termination of the defibrillation shock using at least one second set of electrodes, wherein the first set of electrodes and the second set of electrodes are different sets of electrodes.

21. The cardiac pacing device of claim 17, wherein the defibrillation shock is applied to a heart of a patient using at least one first set of electrodes and wherein the controller circuit is further configured to apply the pacing stimulation signal to the heart of the patient subsequent to termination of the defibrillation shock using at least one second set of electrodes, wherein the first set of electrodes and the second set of electrodes are the same set of electrodes.

22. The cardiac pacing device of claim 17, wherein the controller circuit is further configured to selectively apply paired pacing stimulation to the heart based on at least one of receipt of an external specification and sensed variables associated with cardiac activity.

23. The cardiac pacing device of claim 22, wherein the sensed variables associated with cardiac activity comprise a pulse pressure below a predefined threshold.

24. The cardiac pacing device of claim 22, wherein the external specification comprises instruction from a healthcare provider.

25. The cardiac pacing device of claim 17, wherein the controller circuit is configured to be disposed within an implantable housing for implantation in the patient.

26. The cardiac pacing device of claim 17, wherein the controller circuit is configured to be external to the patient.

27. The cardiac pacing device of claim 17, wherein the defibrillator circuit is further configured to indicate termination of the defibrillation shock to the controller circuit.

28. The cardiac pacing device of claim 17, wherein the defibrillator circuit and the controller circuit are configured to be disposed within an implantable housing for implantation in the patient.

29. The cardiac pacing device of claim 17, wherein the defibrillator circuit and the controller circuit are separate devices.

30. The cardiac pacing device of claim 29, wherein one of the defibrillator circuit and the controller circuit is configured to be disposed within an implantable housing and the other of the defibrillator circuit and the controller circuit is configured to be external to the patient.

31. The cardiac pacing device of claim 17, further comprising at least one set of electrodes for application of the pacing stimulation signal to the heart of the patient.

32. The cardiac pacing device of claim 17, wherein the controller circuit is further configured to apply the pacing stimulation within about one second of termination of the defibrillation shock.

33. The cardiac pacing device of claim 17, wherein the controller circuit is further configured to inhibit application of the pacing stimulation if cardiac activity is detected.

34. The cardiac pacing device of claim 33, wherein the detected cardiac activity comprises a detected blood pressure.

35. The cardiac pacing device of claim 33, wherein the detected cardiac activity comprises spontaneous electrical activity.

36. A cardiac pacing device, comprising: a defibrillator circuit configured to apply a defibrillation shock to the heart of a patient;
a controller circuit configured to automatically apply a pacing stimulation signal to a heart of a patient immediately subsequent to termination of the defibrillation shock by activating one or more electrodes of a first set of electrodes, wherein the controller circuit is further configured to detect cardiac activity and/or function of the heart and select a type of pacing stimulation to apply to the heart of the patient subsequent to termination of the defibrillation shock based on the detected cardiac activity and/or function and automatically apply the selected type of pacing stimulation by activating one or more electrodes of the first set of electrodes, wherein the type of pacing includes a single pacing stimulation comprising a first timing relationship between single pacing pulses and/or or a paired pacing stimulation comprising a second timing relationship between pairs of pacing pulses, and the one or more electrodes of the first set of electrodes activated to apply the pacing stimulation consist only of the same one or more electrodes activated to selectively apply paired pacing stimulation.

37. The cardiac pacing device of claim 36, wherein the controller circuit is further configured to detect the cardiac activity and/or function before applying a defibrillation shock to a heart of the patient.

38. The cardiac pacing device of claim 36, wherein the controller circuit is further configured to detect the cardiac activity and/or function after applying a defibrillation shock to a heart of the patient.

39. A system for cardiac pacing, comprising: a defibrillator circuit configured to apply a defibrillation shock to the heart of a patient;
a first set of electrodes for applying a pacing stimulation to a heart of a patient;
means for automatically applying a pacing stimulation signal to the heart of the patient immediately subsequent to termination of the defibrillation shock by activating one or more electrodes of the first set of electrodes, wherein the pacing stimulation signal comprises single pacing stimulation; and
means for detecting cardiac activity associated with application of the single pacing stimulation; and
means for selectively applying paired pacing stimulation based on the detected cardiac activity by activating one or more electrodes of the first set of electrodes, wherein the single pacing stimulation comprises a first timing relationship between single pacing pulses and the second pacing stimulation comprises a paired timing relationship between pairs of pacing pulses, and the one or more electrodes of the first set of electrodes activated to apply the pacing stimulation consist only of the same one or more electrodes activated to selectively apply paired pacing stimulation.

40. The system of claim 39, wherein the means for automatically applying a pacing stimulation signal comprises means for applying a pacing stimulation signal to the heart of the patient within about two seconds of termination of the defibrillation shock.

41. The system of claim 39, wherein the means for automatically applying a pacing stimulation signal comprises means for applying a pacing stimulation signal to the heart of the patient subsequent to termination of the defibrillation shock irrespective of a characterization of electrical activity detected in the heart.

42. The system of claim 39, wherein the defibrillation shock is applied to a heart of a patient using at least one second set of electrodes; and
wherein the first set of electrodes and the second set of electrodes are different sets of electrodes.

43. The system of claim 39, wherein the defibrillation shock is applied to a heart of a patient using at least one second set of electrodes; and
wherein the first set of electrodes and the second set of electrodes are a same set of electrodes.

44. The system of claim 39, wherein the means for selectively applying further comprises means for selectively applying paired pacing stimulation to the heart based on at least one of receipt of an external specification and sensed variables associated with cardiac activity.

45. The system of claim 44, wherein the sensed variables associated with cardiac activity comprise a pulse pressure below a predefined threshold.

46. The system of claim 44, wherein the external specification comprises instruction from a healthcare provider.

47. The system of claim 39, further comprising means for indicating termination of the defibrillation shock to the means for automatically applying.

48. The system of claim 39, wherein the means for applying a defibrillation shock and the means for automatically applying a pacing stimulation signal are configured to be disposed within an implantable housing for implantation in the patient.

49. The system of claim 39, wherein the means for applying a defibrillation shock and the means for automatically applying a pacing stimulation signal are separate devices.

50. The system of claim 49, wherein one of the means for applying a defibrillation shock and the means for automatically applying a pacing stimulation signal is configured to be disposed within an implantable housing and the other of the means for applying a defibrillation shock and the means for automatically applying a pacing stimulation signal is configured to be external to the patient.

51. The system of claim 39, wherein the means for automatically applying a pacing stimulation signal comprises means for automatically applying a pacing stimulation signal within about one second of termination of the defibrillation shock.

52. The system of claim 39, further comprising means for inhibiting application of the pacing stimulation if cardiac activity is detected.

53. The system of claim 52, wherein the detected cardiac activity comprises a detected blood pressure.

54. The system of claim 52, wherein the detected cardiac activity comprises spontaneous electrical activity.

55. The system of claim 39, wherein the first set of electrodes consists of first and second electrodes.

56. A system for cardiac pacing, comprising: a defibrillator circuit configured to apply a defibrillation shock to the heart of a patient;
a first set of electrodes for applying a pacing stimulation to a heart of a patient;
means for automatically applying a pacing stimulation signal to the heart of the patient immediately subsequent to termination of the defibrillation shock by activating one or more electrodes of the first set of electrodes;
means for detecting cardiac activity and/or function of the heart; and
means for selecting a type of pacing stimulation to apply to the heart of the patient by activating one or more electrodes of the first set of electrodes subsequent to termination of the defibrillation shock based on the detected cardiac activity and/or function, and wherein the means for automatically applying comprises means for automatically applying the selected type of pacing, wherein the type of pacing includes a single pacing stimulation comprising a first timing relationship between single pacing pulses and/or or a paired pacing stimulation comprising a second timing relationship between pairs of pacing pulses, and the one or more electrodes of the first set of electrodes activated to apply the pacing stimulation consist only of the same one or more electrodes activated to selectively apply paired pacing stimulation.

57. The system of claim 56, wherein the means for detecting cardiac activity and/or function comprises means for detecting the cardiac activity and/or function before applying a defibrillation shock to a heart of the patient.

58. The system of claim 56, wherein the means for detecting cardiac activity and/or function comprises means for detecting the cardiac activity and/or function after applying a defibrillation shock to a heart of the patient.

59. The system of claim 56, wherein the selected type of pacing stimulation comprises single pacing stimulation.

60. The system of claim 56, wherein the first set of electrodes consists of first and second electrodes.

61. A computer program product for controlling cardiac pacing, comprising:
a computer readable medium having computer readable program code embodied therein, the computer readable program code comprising: computer readable program code that applies a defibrillation shock to the heart of a patient;
computer readable program code that automatically applies a pacing stimulation signal to the heart of the patient immediately subsequent to termination of the defibrillation shock by activating one or more electrodes of a first set of electrodes, wherein the pacing stimulation signal comprises single pacing stimulation;
computer readable program code that detects cardiac activity associated with application of the single pacing stimulation; and
computer readable program code that selectively applies paired pacing stimulation based on the detected cardiac activity by activating one or more electrodes of the first set of electrodes, wherein the single pacing stimulation comprises a first timing relationship between single pacing pulses and the second pacing stimulation comprises a paired timing relationship between pairs of pacing pulses, and the one or more electrodes of the first set of electrodes activated to apply the pacing stimulation consist only of the same one or more electrodes activated to selectively apply paired pacing stimulation.

62. The computer program product of claim 61, wherein the computer readable program code that automatically applies a pacing stimulation signal comprises computer readable program code that automatically applies a pacing stimulation signal to the heart of the patient within about two seconds of termination of the defibrillation shock.

63. The computer program product of claim 61, wherein the computer readable program code that automatically applies a pacing stimulation comprises computer readable program code that automatically applies a pacing stimulation signal to the heart of the patient subsequent to termination of the defibrillation shock irrespective of a characterization of electrical activity detected in the heart.

64. The computer program product of claim 61, wherein the computer readable program code that selectively applies further comprises computer readable program code that selectively applies paired pacing stimulation to the heart based on at least one of receipt of an external specification and sensed variables associated with cardiac activity.

65. The computer program product of claim 64, wherein the sensed variables associated with cardiac activity comprise a pulse pressure below a predefined threshold.

66. The computer program product of claim 64, wherein the external specification comprises instruction from a healthcare provider.

67. The computer program product of claim 61, further comprising computer readable program code that indicate termination of the defibrillation shock to the computer readable program code that automatically applies.

68. The computer program product of claim 61, further comprising computer readable program code that inhibits application of the pacing stimulation if cardiac activity is detected.

69. The computer program product of claim 68, wherein the detected cardiac activity comprises a detected blood pressure.

70. The computer program product of claim 68, wherein the detected cardiac activity comprises spontaneous electrical activity.

71. A computer program product for controlling cardiac pacing, comprising:

a computer readable medium having computer readable program code embodied therein, the computer readable program code comprising: computer readable program code that applies a defibrillation shock to the heart of a patient;

computer readable program code that automatically applies a pacing stimulation signal to the heart of the patient immediately subsequent to termination of the defibrillation shock by activating one or more electrodes of a first set of electrodes;

computer readable program code that detects cardiac activity and/or function in the heart; and computer readable program code that selects a type of pacing stimulation to apply to the heart of the patient subsequent to termination of the defibrillation shock based on the detected cardiac activity and/or function, and wherein the computer readable program code that automatically applies further comprises computer readable program code that automatically applies the selected type of pacing by activating one or more electrodes of the first set of electrodes, wherein the type of pacing includes a single pacing stimulation comprising a first timing relationship between single pacing pulses and/or or a paired pacing stimulation comprising a second timing relationship between pairs of pacing pulses, and the one or more electrodes of the first set of electrodes activated to apply the pacing stimulation consist only of the same one or more electrodes activated to selectively apply paired pacing stimulation.

72. The computer program product of claim 71, wherein the computer readable program code that detects cardiac activity and/or function comprises computer readable program code that detects the cardiac activity and/or function before applying a defibrillation shock to a heart of the patient.

73. The computer program product of claim 71, wherein the computer readable program code that detects cardiac activity and/or function comprises computer readable program code that detects the cardiac activity and/or function after applying a defibrillation shock to a heart of the patient.

74. The computer program product of claim 71, wherein the selected type of pacing stimulation comprises a combination of single pacing stimulation and paired pacing stimulation.

* * * * *